United States Patent [19]

Edwards

[11] 4,426,379
[45] Jan. 17, 1984

[54] INSECTICIDAL 2-OXO-3-DIALKOXYPHOSPHORO-5-CYCLOPROPYL-1,3,4-OXADIAZOLINE

[75] Inventor: Laroy H. Edwards, Napa, Calif.

[73] Assignee: Chevron Research Company, San Francisco, Calif.

[21] Appl. No.: 343,088

[22] Filed: Jan. 27, 1982

[51] Int. Cl.³ .................. A01N 57/32; C07F 9/65
[52] U.S. Cl. .......................... 424/200; 548/111
[58] Field of Search .................. 548/111; 424/200

[56] References Cited

U.S. PATENT DOCUMENTS 3,523,951  8/1970  Rufenacht .................. 548/111
3,661,926  5/1972  Van Den Bos et al. ......... 548/111
4,202,889  5/1980  Maurer et al. .............. 424/200

FOREIGN PATENT DOCUMENTS 23841  2/1981  European Pat. Off. .

OTHER PUBLICATIONS

Rufenacht, II, Chem. Abst., 1973, vol. 78, No. 97,560d.
Maurer et al., Chem. Abst. 1980, vol. 93, No. 114,559g.
Maurer et al., Chem. Abst. 1980, vol. 93, No. 46822t.

Primary Examiner—Richard Raymond
Attorney, Agent, or Firm—D. A. Newell; T. G. DeJonghe; S. L. Biggs

[57] ABSTRACT

Compounds of the formula

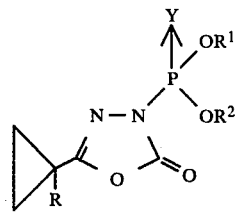

wherein R is hydrogen, lower alkyl or lower alkoxy, $R^1$ and $R^2$ are independently lower alkyl and Y is either oxygen or sulfur possess insecticidal activity.

9 Claims, No Drawings

INSECTICIDAL 2-OXO-3-DIALKOXYPHOSPHORO-5-CYCLOPROPYL-1,3,4-OXADIAZOLINE

BACKGROUND OF THE INVENTION

This invention pertains to new insecticidal compounds.

U.S. Pat. No. 3,661,926 issued to Van den Bos et al discloses 2-oxo-3-dialkoxyphosphoro-5-alkyl (or cycloalkyl of 5 to 7 carbons)-1,3,4-oxadiazolines as insecticidal. U.S. Pat. No. 3,523,951 issued to Rufenacht teaches derivatives of 1,3,4-thiadiazole as possessing insecticidal activity. CA 78:97560d teaches the synthesis of 2-oxo-3-dialkoxyphosphoro-5-alkyl-1,3,4-oxadiazolines.

SUMMARY OF THE INVENTION

The 2-oxo-3-dialkoxyphosphoro-5-cyclopropyl-1,3,4-oxadiazolines of this invention are represented by the formula:

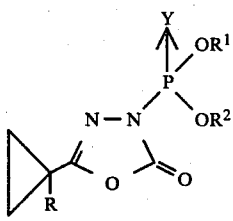

wherein R is hydrogen, lower alkyl or lower alkoxy, $R^1$ and $R^2$ are independently lower alkyl and Y is either oxygen or sulfur.

Among other factors, the present invention is based on my finding that the cyclopropyl derivatives of this invention possess surprisingly superior insecticidal activity against aphids, mites, houseflies, alfalfa weevil and cabbage looper over the cyclohexyl and cyclopentyl derivatives disclosed in U.S. Pat. No. 3,661,926.

A particularly preferred class of compounds in this invention are those where R is lower alkyl. Most preferably, R is methyl.

Preferred $R^1$ and $R^2$ groups are methyl, ethyl and propyl while most preferably $R^1$ and $R^2$ are both ethyl.

Although Y may be both sulfur or oxygen, in the preferred embodiment of this invention, Y is sulfur.

DEFINITIONS

As used herein the following terms have the following meanings, unless expressly stated to the contrary.

The term "alkyl" refers to both straight- and branched-chain alkyl groups. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl and the like.

The term "halo or halogen" refers to the groups fluoro, chloro, bromo and iodo.

The term "alkoxy" refers to the group $R^4O$— wherein $R^4$ is alkyl.

The term "lower alkoxy" refers to alkoxy groups having from 1 through 6 carbon atoms and includes, for example, methoxy, ethoxy, t-butoxy, hexoxy and the like.

The term "phosphoro" refers to the P→O group while the term "thiophosphoro" refers to the P→S group.

The term "dialkoxyphosphoro" refers to the

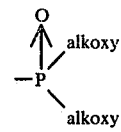

group and includes for example dimethoxyphosphoro

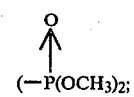

diethoxyphosphoro

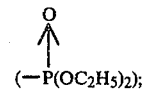

and the like.

The term "dialkoxythiophosphoro" refers to the

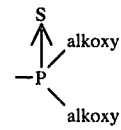

group and includes, for example, dimethoxythiophosphoro, diethoxythiophosphoro and the like.

The term "2-oxo-1,3,4-oxadiazoline" refers to the group:

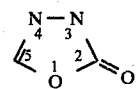

with the conventional numbering system employed, thus the term "2-oxo-3-diethoxythiophosphoro-5-cyclopropyl-1,3,4-oxadiazoline" refers to the group:

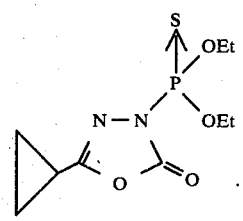

DETAILED DESCRIPTION OF THE INVENTION

The compounds of this invention may be prepared according to the synthetic scheme shown below:

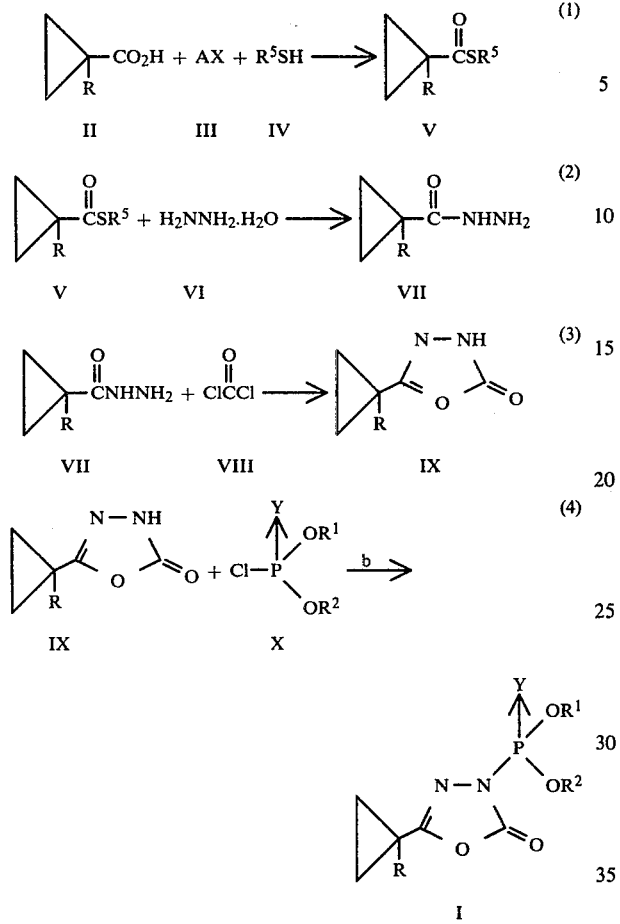

wherein R, $R^1$, $R^2$ and Y are as defined above, $R^5$ is lower alkyl, AX is a halogenating agent, X is a halogen, and b is a base.

Reaction 1 is conducted by initially adding at 0°–5° C. an essentially equimolar amount of a halogenating agent, III, to II. Any halogenating agent such as thionyl chloride, oxalyl chloride and the like which is capable of converting a carboxylic acid to an acid halide may be used although thionyl chloride is preferred. The reaction is done in the liquid phase using an inert anhydrous organic solvent such as diethyl ether, chloroform, methylene chloride, and the like. After addition, the system is then heated to reflux. Reaction pressure is not critical and for convenience the reaction is conducted at atmospheric pressure. After heating at reflux for from 1 to 24 hours, the system is cooled to 0°–5° C. An essentially equimolar amount of an alkyl mercaptan (IV), preferably ethyl mercaptan, is then added. The system is stirred at reflux for from 1 to 24 hours and then at room temperature for an additional 1 to 48 hours. As before, reaction pressure is not critical at this step and for convenience the reaction is conducted at atmospheric pressure. The product V is then isolated by conventional procedures such as extraction, filtration, chromatography, distillation or alternatively is used directly in reaction 2 without purification and/or isolation.

In reaction 2, the thioester, V, is added at 0°–5° C. to approximately 1.5 equivalents of VI. The reaction is done in the liquid phase using a solution of alcohol and water as the solvent. Although various concentrations of alcohol to water may be used the preferred solution is approximately 8:1 alcohol to water. The preferred alcohol in this reaction is methanol although other alcohols such as ethanol, isopropanol and the like may be used. The reaction is conducted at from 0°–50° C. although preferably at from 0°–5° C. Reaction pressure is not critical and for convenience the reaction is conducted at atmospheric pressure. The reaction is generally complete within 1 to 48 hours. The product VII is then isolated by conventional procedures such as extraction, filtration, chromatography, distillation or alternatively is used directly in reaction 3 without purification and/or isolation.

Reaction 3 is conducted by adding approximately 0.6 to 1.1 equivalents of phosgene VIII to VII. The reaction is done in the liquid phase using an inert organic solvent such as methylene chloride, chloroform, toluene and the like. Reaction pressure is not critical and for convenience the reaction is conducted at atmospheric pressure. After addition, the reaction is heated at reflux. Generally, the reaction is complete within 1 to 20 hours. The product IX is then isolated by conventional procedures such as extraction, filtration, chromatography, distillation or alternatively is used directly in reaction 4 without purification and/or isolation.

In reaction 4, the 2-oxo-5-cyclopropyl-1,3,4-oxadiazoline is treated with a substantially equimolar amount of either dialkoxychlorothiophosphate or dialkoxychlorophosphate, X. The reaction is conducted in the liquid phase using an organic solvent such as ethanol, acetone, dimethoxyethane, dimethylformamide, methanol, and the like. Between 1 and 2 equivalents of an organic or inorganic base is added to the system to scavenge the acid generated by the reaction. Preferably, an inorganic base such as potassium carbonate, potassium bicarbonate, sodium hydride and the like is used. Most preferably, the reaction is conducted using potassium carbonate in an acetone medium. Reaction pressure is not critical and for convenience the reaction is conducted at atmospheric pressure. The reaction is heated at reflux and is generally complete within 1 to 24 hours. The 2-oxo-3-dialkoxyphosphoro (dialkoxythiophosphoro)-5-cyclopropyl-1,3,4-oxadiazoline, product I, is isolated by conventional procedures such as extraction, filtration, chromatography, or distillation.

Utility

The compounds of this invention are useful for controlling certain insects. Particularly such insects as aphids (*Aphis gossypii ni*), cabbage looper (*Trichophisia ni*), american cockroach (*Periplaneta americana L.*), alfafa weevil (*H. brunneipennis Boheman*), housefly (*Musca domestica L.*) and mites (*Tetramuchus urticae*). However, some insecticidal compounds of this invention may be more insecticidally active than others against particular pests.

Like most insecticides, they are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5% to 80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in insecticidal formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the toxicant with a liquid or solid emulsifying agent, or may also contain a liquid carrier, such as xylene, heavy aromatic naphthas, isophorone, and other non-volatile organic solvents. For application, these concentrates are dispersed in water or other liquid carrier, and normally applied as a spray to the area to be treated.

Other useful formulations for insecticidal applications include simple solutions of the active ingredient in a dispersant in which it is completely soluble at the desired concentration, such as acetone, alkylated naphthalenes, xylene, or other organic solvents. Granular formulations wherein the toxicant is carried on relatively coarse particles, are of particular utility for aerial distribution or for penetration of cover-crop canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the Freons, may also be used. All of these techniques for formulating and applying the active ingredient are well known in the art.

The percentages by weight of the toxicant may vary according to the manner in which the composition is to be applied and the particular type of formulation, but in general comprises 0.1% to 95% of the toxicant by weight of the insecticidal composition.

The insecticidal compositions may be formulated and applied with other active ingredients, including nematocides, insecticides, fungicides, bactericides, plant growth regulators, fertilizers, etc. In applying the chemical an effective amount and concentration of the toxicants of this invention is, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms, and the like.

A further understanding of the invention can be had in the following nonlimiting examples, wherein, unless expressly stated to the contrary, all temperatures and temperature ranges refer to the Centigrade system and the term "ambient" or "room temperature" refers to about 20°-25° C. The term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly isomer mixtures are obtained as products.

Other compounds which were prepared in accordance with Examples 1 to 4 below are listed in Table I.

EXAMPLE 1

Preparation of 1-methylcyclothiopropanoic Acid Ethyl Ester 100 gm of 1-methylcyclopropanoic acid was added to 150 ml of diethyl ether. The system was cooled to 0°-5° C. and 119 gm of thionyl chloride was added dropwise over a period of time. After addition, the system was heated at reflux for 8 hours. The system was then cooled to 0°-5° C. and 62 gm of ethanethiol was added dropwise. The system was heated at reflux for 6 hours and then stirred at room temperature for 72 hours. The diethyl ether was removed by stripping to give the 1-methylcyclopropanoic acid ethyl ester.

EXAMPLE 2

Preparation of 2-oxo-5-(1'-methylcyclopropyl)-1,3,4-oxadiazoline (a) 48 gm (approximately 1.5 equivalents) of hydrazine was first added to 80 ml of methanol and 12 ml of water was then added to the system. Afterwards, the 1-methylcyclopropanoic ethyl ester of Example 1 was added dropwise to the system at 0°-5° C. The system was then stirred overnight. The solvent was removed by stripping. The product was dissolved in methylene chloride and then dried over magnesium sulfate. The methylene chloride was removed by stripping to give 85 gm of 1-methylcyclopropane carboxylic acid hydrazide.

(b) 85 gm of 1-methylcyclopropane carboxylic acid hydrazide was added to methylene chloride on a 3-neck 2-liter round bottom flask. The system was first cooled to 0°-5° C. and 590.5 gm of a 12.5% solution of phosgene added dropwise over a period of time. The system was then heated at reflux for 7 hours. The methylene chloride was removed by stripping. The product was washed with petroleum ether and filtered to give 66.6 gm of 2-oxo-5-(1'-methylcyclopropyl)-1,3,4-oxadiazoline as light brown crystals, m.p. 68°–70° C.

EXAMPLE 3

Preparation of 2-oxo-3-diethoxy-phosphoro-5-(1'-methylcyclopropyl)-1,3,4-oxadiazoline 2-oxo-5-(1'methylcyclopropyl)-1,3,4-oxadiazoline, 15 gm is added to 150 ml of dimethoxyethane. 3.6 gm of a 60% concentration of sodium hydride is slowly added. The system is refluxed for 1 hour and then cooled to room temperature. 19.3 gm of diethoxychlorophosphate is then added. The system is heated at reflux for 2½ hours and then stirred at room temperature for 12 hours. The system is then again heated to reflux for an additional 1½ hours. The system is then washed with water. The product is extracted with methylene chloride. The methylene chloride solution is dried over magnesium sulfate and stripped to give the crude product. The product is purified by chromatography using 50–200 mesh silica and 1:1 methylene chloride to petroleum ether as the elutant to give the 2-oxo-3-diethoxyphosphoro-5-(1'methylcyclopropyl)-1,3,4-oxadiazoline.

EXAMPLE 4

Preparation of 2-oxo-3-diethoxythiophosphoro-5-(1'-methylcyclopropyl)-1,3,4-oxadiazoline 2-oxo-5-(1'-methylcyclopropyl)-1,3,4-oxadiazoline, 10.0 gm, was added to 100 ml of dimethoxyethane. 2.4 gm of a 60% concentration of sodium hydride was slowly added. The system was refluxed for 1 hour and then cooled to room temperature. 13.2 gm of diethoxychlorothiophosphate was then added. The system was heated at reflux for 2½ hours and then stirred at room temperature for 12 hours. The system was then again heated to reflux for an additional 1½ hours. The system was then washed with water. The product was extracted with methylene chloride. The methylene chloride solution was dried over magnesium sulfate and stripped to give as a crude product the 2-oxo-3-diethoxythiophosphoro-5-(1'-methylcyclopropyl)-1,3,4-oxadiazoline. This product was purified by chromatography using 50–200 mesh silica and 1:1 methylene chloride to petroleum ether as elutant.

Examination by IR and NMR spectroscopy was in complete accord with the proposed structure. This product is listed as compound number 5 in Table I.

Representative compounds of this invention which are prepared in accordance with Examples 1 to 4 above include for instance:

2-oxo-3-dimethoxythiophosphoro-5-cyclopropyl-1,3,4-oxadiazoline;
2-oxo-3-diethoxythiophosphoro-5-cyclopropyl-1,3,4-oxadiazoline;
2-oxo-3-dimethoxythiophosphoro-5-(1'-methylcyclopropyl)-1,3,4-oxadiazoline;
2-oxo-3-diethoxythiophosphoro-5-(1'-methylcyclopropyl)-1,3,4-oxadiazoline;
2-oxo-3-dimethoxythiophosphoro-5-(1'-ethylcyclopropyl)-1,3,4-oxadiazoline;
2-oxo-3-diethoxythiophosphoro-5-(1'-ethylcyclopropyl)-1,3,4-oxadiazoline;
2-oxo-3-diethoxythiophosphoro-5-(1'-hexoxycyclopropyl)-1,3,4-oxadiazoline;
2-oxo-3-dimethoxythiophosphoro-5-(1'-hexoxycyclopropyl)-1,3,4-oxadiazoline;
2-oxo-3-dimethoxythiophosphoro-5-(1'-methoxycyclopropyl)-1,3,4-oxadiazoline;
2-oxo-3-dimethoxythiophosphoro-5-(1'-ethoxycyclopropyl)-1,3,4-oxadiazoline;
2-oxo-3-diethoxythiophosphoro-5-(1'-methoxycyclopropyl)-1,3,4-oxadiazoline;
2-oxo-3-diethoxythiophosphoro-5-(1'-methoxycyclopropyl)-1,3,4-oxadiazoline;
2-oxo-3-dimethoxyphosphoro-5-cyclopropyl-1,3,4-oxadiazoline;
2-oxo-3-diethoxyphosphoro-5-cyclopropyl-1,3,4-oxadiazoline;
2-oxo-3-dimethoxyphosphoro-5-(1'-methylcyclopropyl)-1,3,4-oxadiazoline;
2-oxo-3-diethoxyphosphoro-5-(1'-methylcyclopropyl)-1,3,4-oxadiazoline;
2-oxo-3-dimethoxyphosphoro-5-(1'-ethylcyclopropyl)-1,3,4-oxadiazoline;
2-oxo-3-diethoxyphosphoro-5-(1'-ethycyclopropyl)-1,3,4-oxadiazoline;
2-oxo-3-diethoxyphosphoro-5-(1'-hexoxycyclopropyl)-1,3,4-oxadiazoline;
2-oxo-3-dimethoxyphosphoro-5-(1'-hexylcyclopropyl)-1,3,4-oxadiazoline;
2-oxo-3-dimethoxyphosphoro-5-(1'-hexoxycyclopropyl)-1,3,4-oxadiazoline;
2-oxo-3-dimethoxyphosphoro-5-(1'-methoxycyclopropyl)-1,3,4-oxadiazoline;
2-oxo-3-dimethoxyphosphoro-5-(1'ethoxycyclopropyl)-1,3,4-oxadiazoline;
2-oxo-3-diethoxyphosphoro-5-(1'-methoxycyclopropyl)-1,3,4-oxadiazoline;
2-oxo-3-diethoxyphosphoro-5-(1'-ethoxycyclopropyl)-1,3,4-oxadiazoline;

EXAMPLE 5

Aphid Control

The compounds of the invention were tested for their insecticidal activity against cotton aphids (*Aphis gossypii* Glover). An acetone solution of the candidate toxicant containing a small amount of nonionic emulsifier was diluted with water to 40 ppm. Cucumber leaves infested with the cotton aphids were dipped in the toxicant solution. Mortality readings were taken after 24 hours. The results are tabulated in Table II in terms of percent control

EXAMPLE 6

Cabbage Looper Control

The compounds of the invention were tested for their insecticidal activity against Cabbage Looper (*Trichoplusia ni*). An acetone solution of the candidate toxicant containing a small amount of nonionic emulsifier was diluted with water to 500 ppm. Excised cucumber leaves were dipped in the toxicant solution and allowed to dry. They were then infested with Cabbage Looper larvae. Mortality readings were taken after 24 hours. The results are tabulated in Table II in terms of percent control.

EXAMPLE 7

American Cockroach

American Cockroach (*Periplaneta americana L.*): A 500 ppm acetone solution of the candidate toxicant was placed in a microsprayer (atomizer). A random mixture of anesthetized male and female roaches was placed in a container and 55 mg of the above-described acetone solution was sprayed on them. A lid was placed on the container. A mortality reading was made after 24 hours. The results are tabulated in Table II in terms of percent control.

EXAMPLE 8

Alfalfa Weevil

Alfalfa Weevil (*H. brunneipennis Boheman*): A 500 ppm acetone solution of the candidate toxicant was placed in a microsprayer (atomizer). A random mixture of anesthetized male and female flies was placed in a container and 55 mg of the above-described acetone solution was sprayed on them. A lid was placed in the container. A mortality reading was made after 24 hours. The results are tabulated in Table II in terms of percent control.

EXAMPLE 9

Housefly

Housefly (*Musca domestica L.*): A 500 ppm acetone solution of the candidate toxicant was placed in a microsprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table II in terms of percent control.

EXAMPLE 10

Mites

Two-spotted Mite (*Tetramuchus urticae*): An acetone solution of the candidate toxicant containing a small amount of nonionic emulsifier was diluted with water to 40 ppm. Lima bean leaves which were infested with mites were dipped in the toxicant solution. Mortality readings were taken after 24 hours. The results are tabulated in Table II in terms of percent control.

EXAMPLE 11

Aphids Systemic Evaluation

This procedure is used to assess the ability of a candidate insecticide to be absorbed through the plant root system and translocate to the foliage 2 cucumber plants planted in a 4 inch fiber pot with a soil surface area of 80 cm$^2$ are used. 40 ml of an 80 ppm solution of the candidate insecticide is poured around the plants in each pot. (This corresponds to 40/cm$^2$ of actual toxicant.) The plants are maintained throughout in a greenhouse at 75° to 85° F. 48 hours after the drenching, the treated plants are infested with aphids by placing well colonized leaves over the treated leave so as to allow the aphids to migrate easily from the infested leaf to the treated leaf. Three days after infestation, mortality readings were taken. The results are tabulated in Table II in terms of percent control.

I

COMPOUNDS OF THE FORMULA

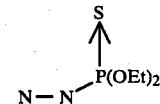

| Compound No. | R | Carbon Calc. | Carbon Fd. | Hydrogen Calc. | Hydrogen Fd. | Nitrogen Calc. | Nitrogen Fd. | State |
|---|---|---|---|---|---|---|---|---|
| 1 | (CH$_3$)$_3$C— | 40.81 | 38.72 | 6.51 | 6.55 | 9.52 | 8.19 | oil |
| 2 | cyclohexyl-CH$_3$ | 46.70 | 45.63 | 6.93 | 7.16 | — | — | oil |
| 3 | cyclohexyl | 44.99 | 41.37 | 6.61 | 6.29 | 8.74 | 8.05 | oil |
| 4 | cyclopropyl | 38.85 | 35.52 | 5.43 | 5.15 | 10.07 | 9.10 | oil |
| 5 | isopropyl-CH$_3$ | 41.09 | 41.51 | 5.86 | 6.28 | 9.58 | 10.02 | oil |
| 6 | cyclopentyl | 43.13 | 44.38 | 6.25 | 6.64 | 9.15 | 9.29 | oil |
| 7 | —CH$_2$C(CH$_3$)$_3$ | 42.85 | 41.92 | 6.86 | 6.85 | 9.09 | 9.17 | oil |

I-continued

COMPOUNDS OF THE FORMULA

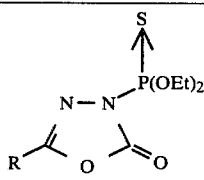

| Compound No. | R | ANALYSIS | | | | | | State |
|---|---|---|---|---|---|---|---|---|
| | | Carbon | | Hydrogen | | Nitrogen | | |
| | | Calc. | Fd. | Calc. | Fd. | Calc. | Fd. | |
| 8 | CH$_3$<br>$\|$<br>—C—SCH$_3$<br>$\|$<br>CH$_3$ | 36.80 | 37.33 | 5.87 | 6.24 | 8.58 | 8.84 | oil |
| 9 | —CH$_2$OCH$_3$ | 34.04 | 36.81 | 5.36 | 5.92 | 9.93 | 10.58 | oil |

TABLE II

| | Aphids[1] | Aphids Sys.[1a] | Mites Ad.[2] | % CONTROL Housefly[3] | Am. Roach[4] | Alf. Weevil[5] | Cab. Looper[6] |
|---|---|---|---|---|---|---|---|
| 1 | 99 | 0 | 0 | 100 | 100 | 10 | 80 |
| 2 | 100 | 0 | 0 | 70 | 99 | 20 | 10 |
| 3 | 78 | 0 | 0 | 60 | 98 | 20 | 10 |
| 4 | 100 | 0 | 70 | 100 | 100 | 100 | 80 |
| 5 | 100 | 90 | 99 | 100 | 100 | 80 | 100 |
| 6 | 0 | 0 | 0 | 39 | 100 | 0 | 50 |
| 7 | 100 | 0 | 15 | 99 | 100 | 60 | 60 |
| 8 | 100 | 0 | 96 | 39 | 100 | 70 | 0 |
| 9 | 100 | 0 | 0 | 98 | 100 | 50 | 20 |

[1] Aphids — *Aphis gossypii* Glover
[1a] Aphids Sys. — Aphids Systmeic Evaluation
[2] Mites — *Tetramuchus urtical*
[3] Housefly — *Musca domestica* L.
[4] American Cockroach — *Periplaneta americana* L.
[5] Alfalfa Weevil — *H. brunneipennis* Bohemian
[6] Cabbage Looper — *Trichoplusia ni*

I claim:
1. A compound of the formula

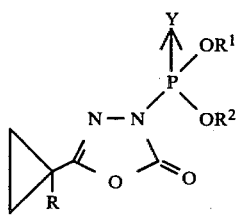

where R is hydrogen, lower alkyl or lower alkoxy, R$^1$ and R$^2$ are independently lower alkyl and Y is either oxygen or sulfur.

2. A compound of the formula defined in claim 1 wherein R$^1$ and R$^2$ are ethyl.

3. A compound of the formula defined in claim 2 wherein Y is sulfur.

4. A compound of the formula defined in claim 3 wherein R is methyl.

5. A compound of the formula defined in claim 3 wherein R is hydrogen.

6. A method of killing insects comprising contacting said insects or their habitats with an insecticidally effective amount of a compound of the formula defined in claim 1.

7. A method of killing insects comprising contacting said insects or their habitats with an insecticidally effective amount of a compound of the formula defined in claim 4.

8. An insecticidal composition comprising a biologically inert carrier and an insecticidally effective amount of a compound of the formula defined in claim 1.

9. An insecticidal composition comprising a biologically inert carrier and an insecticidally effective amount of a compound of the formula defined in claim 4.

* * * * *